United States Patent [19]
Wilting et al.

[11] Patent Number: 6,094,468
[45] Date of Patent: Jul. 25, 2000

[54] ADJUSTABLE COMPUTER TOMOGRAPHY DEVICE

[75] Inventors: Jantje E. Wilting; Jan Timmer; Fransisca M. C. De Brouwer, all of Eindhoven, Netherlands

[73] Assignee: U.S. Philips Corporation, New York, N.Y.

[21] Appl. No.: 09/103,735

[22] Filed: Jun. 24, 1998

[30] Foreign Application Priority Data

Jun. 26, 1997 [EP] European Pat. Off. .............. 97201958

[51] Int. Cl.[7] ........................................ A61B 6/03
[52] U.S. Cl. ................................. 378/8; 378/16
[58] Field of Search ..................... 378/8, 16, 95, 378/97, 108

[56] References Cited

U.S. PATENT DOCUMENTS

| | | | |
|---|---|---|---|
| Re. 35,848 | 7/1998 | Tanaka | 378/16 |
| 5,103,469 | 4/1992 | Tanaka | 378/16 |
| 5,231,651 | 7/1993 | Ozaki et al. | 378/4 |
| 5,379,333 | 1/1995 | Toth | 378/16 |
| 5,400,378 | 3/1995 | Toth | 378/16 |
| 5,629,971 | 5/1997 | Jones et al. | 378/145 |
| 5,737,386 | 4/1998 | Strawder | 378/95 |

*Primary Examiner*—David P. Porta
*Attorney, Agent, or Firm*—Dwight H. Renfrew

[57] ABSTRACT

A computer tomography device includes an X-ray source (1) and an X-ray detection system (3) for forming a number of density profiles of an object to be radiologically examined. A reconstruction unit (4) derives an image signal from the density profiles. A control system (20) adjusts the X-ray source (1) on the basis of a density value of the object and the control system is arranged to adjust the X-ray source on the basis of a part of the object to be examined. The control system is also arranged to adjust the X-ray source on the basis of a reference adjustment of the X-ray source. The reference adjustment is dependent on the part of the object to be examined.

17 Claims, 1 Drawing Sheet

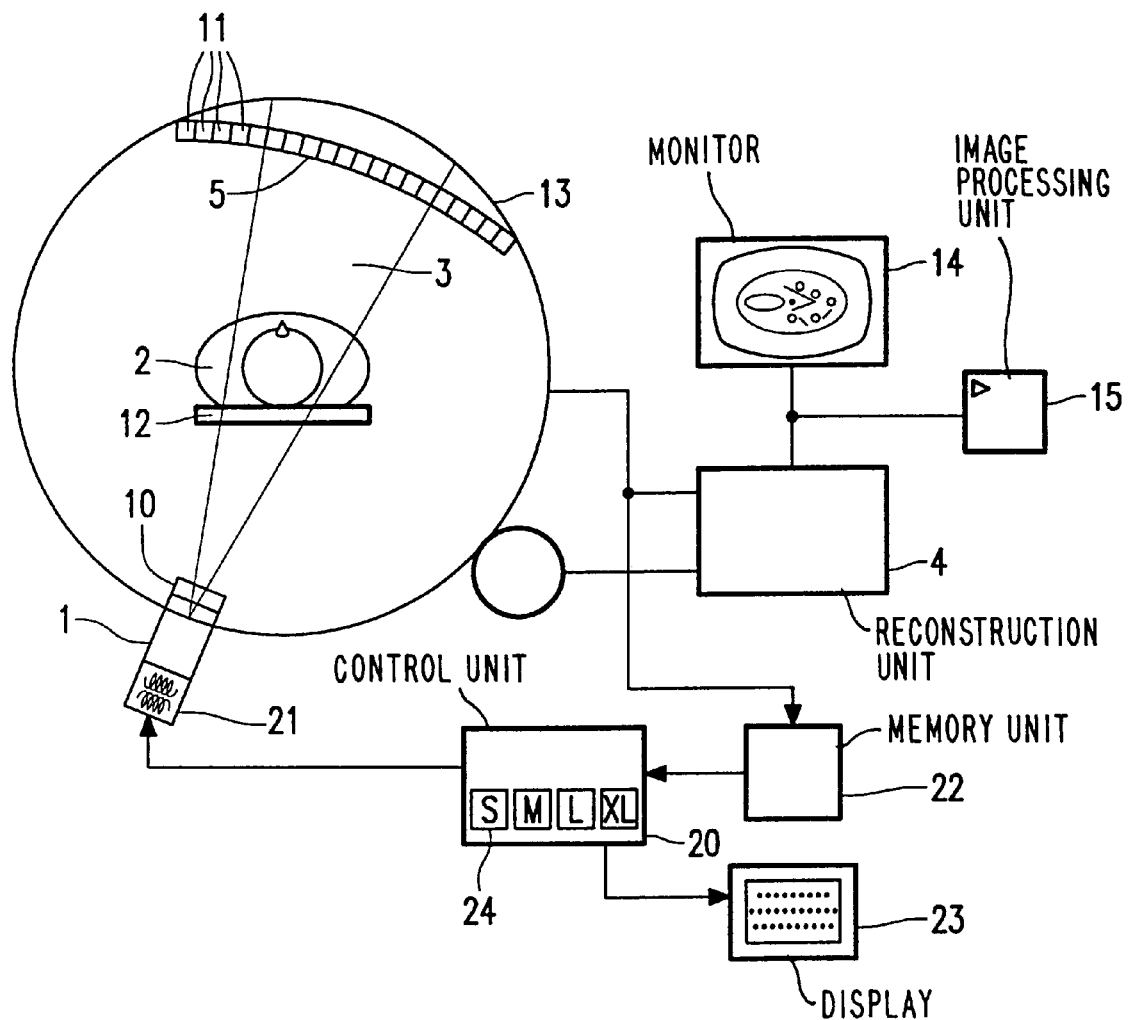

ADJUSTABLE COMPUTER TOMOGRAPHY DEVICE

BACKGROUND OF THE INVENTION

1. Field of the Invention

The invention relates to a computer tomography device, including an X-ray source, an X-ray detection system for picking up a number of density profiles of an object to be radiologically examined, a reconstruction unit for deriving an image signal from the density profiles, and a control system for adjusting the X-ray source on the basis of a density value of the object. This invention also relates to a method of computer tomography.

2. Description of the Related Art

A computer tomography device of this kind is known from United States patent U.S. Pat. No. 5,400,378.

The control system of the known computer tomography device adjusts the tube current of the X-ray source on the basis of relative X-ray absorption values derived from "scout data". The "scout data" represent the attenuation of X-rays in the object relative to a standard value. Such scout data comprises the minimum values of two density profiles picked up by exposing the object to be examined to X-rays from two mutually perpendicular directions. The tube current is adjusted on the basis of the relative X-ray absorption values. In the known computer tomography device the adjustment of the X-ray source is adapted to the relative X-ray absorption in the part of the object to be examined, for example a patient to be radiologically examined. However, the control system does not suitably take into account the fact that the desired image quality differs for images of different parts of the object to be examined.

The density profiles are picked up by irradiating the patient by means of X-rays from a number of directions. An image of, for example a cross-section of the object is reconstructed from the density profiles. The operation of the known computer tomography device is also known from the general article "X-ray computed tomography for medical imaging" by Harish P. Hiriyannaiah in IEEE Signal Processing Magazine, March 1997, pp. 42–59.

SUMMARY OF THE INVENTION

It is an object of the invention to provide a computer tomography device for forming an image of high diagnostic quality while limiting the X-ray dose whereto the patient is exposed.

This object is achieved by means of a computer tomography device according to the invention which is characterized in that the control system is arranged to adjust the X-ray source on the basis of a kind of tissue of a part of the object to be examined.

The intensity and/or energy of the X-rays can be accurately adapted to the part of the object to be examined. The intensity and/or energy of the X-rays can notably be adapted very well to the anatomy and the morphology of the patient to be examined, thus ensuring that an image of high diagnostic quality is formed whereas the X-ray dose whereto the patient is exposed remains comparatively low. An image of high diagnostic quality notably has a low noise level, so that small details of low contrast can still be reproduced in a suitably visible manner. The intensity and/or energy of the X-rays is adjusted to be as low as possible, but high enough to ensure that the noise level of the image is acceptably low. Notably, the intensity and/or energy of the x-rays is adjusted on the basis of the morphology of the part of the patient's anatomy to be examined. The X-ray source is adjusted so that it yields an image having the quality required for the part imaged. Image quality relates notably to the noise level of the image, the contrast of the image, and their mutual relationship which represents the contrast resolution. The contrast resolution is the smallest brightness difference in the image of a detail of given dimensions which can still be visibly reproduced. Notably the noise level, or rather the contrast resolution, is adapted to the part of the anatomy of the patient to be examined. Particularly the imaging of lung tissue requires only little contrast resolution, because small deviations can be readily noticed in the image against the background of low X-ray absorption. When liver tissue is imaged, it is necessary to form an image having a high contrast resolution so as to enable detection of anomalies with a small density difference relative to the surroundings. It has been found that the contrast resolution is related to the noise level of the image. For individual adjustments of parameters concerning the picking up of the density profiles, notably the slice thickness the tube current and the high voltage of the x-ray source and adjustments of electronic signal filters in the reconstruction unit and/or the adjustment of X-ray filters in the X-ray beam, the contrast resolution is a function of the noise level. It has been found that the noise level of the image can be readily predicted as a function of the adjustment of the X-ray source; this is because the noise in the image is caused mainly by shot noise of the X-rays, said shot noise having a Poisson distribution.

The intensity of the X-rays can be readily adjusted by adjustment of the tube current of the X-ray source. The tube current is the electric current of an electron beam by which X-rays are generated in an anode of the X-ray source. The energy of the X-rays can be readily adjusted by adjustment of the electric high voltage between the cathode and the anode of the X-ray tube. Furthermore, the period of time during which the X-ray source emits X-rays can also be adjusted. This period of time is the pulse duration of the X-ray pulses produced by the X-ray source. The product of the tube current and the pulse duration is also referred to as the mAs value. This mAs value represents the X-ray dose to which the patient is exposed. Furthermore, the energy of the X-rays can be adjusted by adaptation of the electric high voltage applied to the X-ray source.

For the adjustment of the X-ray source the control system preferably takes into account a density value of the object and a reference adjustment. The density value differs for each part of the anatomy to be examined; for example, lung tissue absorbs hardly any X-rays whereas the skull and the region of the hips absorb a comparatively large amount of X-rays. The reference adjustment concerns an adjustment which yields, in a rather large number of situations, an image of acceptable image quality while exposing the patient to an acceptable X-ray dose. For example, the reference adjustment is an adjustment of the X-ray source which yields the desired result for a majority of patients undergoing the relevant radiological examination, a group of patients having a diameter in a predetermined range or the reference adjustment is an adjustment which is adequate for a radiological examination of a voluminous patient. The reference adjustment is preferably dependent on the part of the anatomy to be examined, on the expected pathology or on the diagnostic requirements. Preferably, the reference adjustment is used, or the radiologist is at least offered the possibility of selecting the reference adjustment, when an adjustment derived by the control system does not lead to a substantial reduction of the required X-ray dose.

The adjustment which is co-based on the reference adjustment and the density value, however, can also be suitably used without taking into account the part of the patient to be examined for the adjustment.

The reference adjustment preferably takes into account the fact that a different image quality is required for the imaging of different parts of the anatomy. Preferably, the reference adjustment is chosen so that it yields the desired quality when a comparatively voluminous patient is examined. The adjustment of the X-ray source can be readily adapted to the patient to be examined. The reference adjustment can also be derived from a mean or representative volume of the relevant part of the anatomy to be examined, the density or the X-ray absorption of said part and the desired image quality also being taken into account.

In an embodiment of a computer tomography device according to the invention, the control system takes into account a difference between the adjustment derived by the control system and the reference adjustment. The adjustment of the X-ray source preferably is changed only if a patient is examined whose build deviates significantly from the build associated with the reference adjustment. It is thus achieved that most radiological examinations are performed on the basis of a standardized protocol. Moreover, the loss of a substantial amount of time for readjustment of the X-ray source is avoided. Furthermore, the adjustment of the X-ray source will not be influenced by inaccuracies occurring during extraction of the adjustment of the X-ray source. Preferably, the adjustment of the X-ray source is adapted, so as to limit the X-ray dose to which a patient is exposed, only in the case of particularly large or voluminous patients, particularly small or skinny patients or children. To this end, the control system changes the adjustment of the X-ray source if the adjustment derived by the control system deviates from the reference adjustment by more than a threshold value. The threshold value can be adjusted in advance. In practice, preferably a threshold value is used which yields a reduction of the X-ray dose by approximately ⅓ relative to the X-ray dose associated with the relevant reference adjustment.

In an embodiment of a computer tomography device according to the invention the difference between the adjustment derived by the control system and the reference adjustment is displayed. This enables the radiologist to adjust the X-ray source by hand, on the basis of the adjustment advised by the control system, or to use the reference adjustment.

In an embodiment of a computer tomography device according to the invention, the adjustment of the X-ray source concerns the intensity and/or the energy of the X-rays emitted by the X-ray source. The intensity of the X-ray source can be readily adjusted by controlling the tube current of the X-ray source. The energy of the X-ray source can be readily adjusted by controlling the electric high voltage of the X-ray source.

In an embodiment of a computer tomography device according to the invention, the density value of the patient to be examined can be readily measured, notably locally, by irradiating the patient by means of X-rays and by locally detecting to what extent the X-rays are attenuated. The result of such a measurement is referred to as a "scanogram" or "scout data". Preferably, the X-ray source irradiates the patient by means of X-rays while the X-ray source and the X-ray detector are maintained in a fixed orientation relative to the patient. The X-ray source thus forms an X-ray shadow image which is usually called a "scanogram". The scanogram is usually employed to select a part of the patient of which density profiter are to be picked up. The local dimension of the patient, notably the thickness, can be accurately derived from the scanogram. According to the invention, for the formation of the scanogram the X-ray source is adjusted while taking into account the dimensions of the patient. In order to form a scanogram of a skinny patient, the intensity and/or the energy of the X-rays is chosen to be lower whereas in order to form a scanogram of a heavier or very heavy patient a higher intensity and/or energy of the X-rays is selected. In order to make a scanogram of a small child, preferably a very low intensity and/or energy of the X-rays is used. It has been found that in order to form the scanogram the X-ray source can be sufficiently accurately adjusted on the basis of a coarse judgement of the patient. Such a coarse judgement of the patient can be readily made in a glance. It also makes sense to form such a scanogram while taking into account a property of the patient to be examined, for example the stature thereof, independently of the use of the scanogram for adjusting the X-ray source.

In an embodiment of a computer tomography device according to the invention, the patient is exposed to a lower X-ray dose by reducing the intensity and/or energy of the X-ray source. Moreover, when the tube current is reduced, no problems are encountered in respect of the cooling of the X-ray source and the stability of the intensity and the energy of the emitted X-rays. The reference adjustment preferably concerns the adjustment which is adequate for a radiological examination of a voluminous patient, so that the X-ray dose to which a patient is exposed in practice is practically always lower than the X-ray dose that would be applied according to the reference adjustment.

An embodiment of a computer tomography device according to the invention in which a noise index is used is defined in claim 9. The noise index represents the amount of noise to be expected in the image in dependence on the adjustment of the computer tomography device. By selecting a value of the noise index, the radiologist provides an indication as to which noise impression is desired for the image to be generated. The control system derives an adjustment of the X-ray source from the value selected for the noise index so as to achieve the desired image quality.

The noise index is defined in such a manner that a strong correlation exists between a more or less subjective evaluation of noise by the radiologist and the objective value of the standard deviation of the brightness values of the image. The standard deviation represents variations of the brightness values in as far as they do not relate to image information.

In an embodiment of a computer tomography device according to the invention, the angle at which the patient is irradiated can thus be taken into account. As the angle of incidence of the X-rays is larger, the path traveled by the X-rays through the patient will be longer and the X-rays will be attenuated more. It is also an object of the invention to provide a method of computed tomography for forming an image of high diagnostic quality while limiting the x-ray dose whereto the patient is exposed.

BRIEF DESCRIPTION OF THE DRAWING

These and other aspects of the invention will be described in detail hereinafter with reference to the following embodiments and the accompanying drawing; therein:

The FIGURE shows diagrammatically a computer device according to the invention.

DESCRIPTION OF THE PREFERRED EMBODIMENT

The FIGURE shows diagrammatically a computer tomography device according to the invention. An X-ray source 1 co-operates with a slit-shaped diaphragm 10 so as to emit a diverging flat (fan-shaped) X-ray beam 3 for irradiating the object 2, for example a patient to be examined. The X-ray detector 5 is arranged opposite the X-ray source 1. The X-ray detector of the present embodiment is a position-sensitive X-ray detector which comprises a row of separate detector cells 11. The detector cells 11 are, for example gas-filled (xenon) detectors or solid-state detectors. The thickness of the fan-shaped X-ray beam generally amounts to from 1 mm to 10 mm, measured halfway between the X-ray source and the X-ray detector. The intensity of the radiation having traversed the patient and incident on the X-ray detector is determined mainly by the absorption within the patient 2 who is arranged on a table 12 between the X-ray source and the X-ray detector. The absorption is measured along a large number of lines from a large number of directions by rotating the X-ray source 1 and the X-ray detector 5 together around the patient by means of a support 13. The combined rotation of the X-ray source and the X-ray detector may be continuous but also intermittent. Furthermore, the patient can be displaced along the axis of rotation during irradiation and rotation, so that the X-ray detector acquires data from a significant three-dimensional volume of the patient. In addition to a rotatable assembly with an X-ray source and an X-ray detector, the computer device may also include a detection system which is not rotatable but extends along (substantially) the entire circumference of the patient. Generally speaking, the X-ray source and the X-ray detector are fully rotated together, i.e. through 360°, around the patient. Alternatively, use can be made of a detection system which extends along the entire circumference of the patient; in that case the X-ray source is rotated completely around the patient. Furthermore, an annular anode arranged around the patient can also be used as the X-ray source, the point of incidence of an electron beam generating X-rays from the anode material then being displaced along the annular anode around the patient. It suffices in principle, however, to use a fan-shaped beam which rotates around the patient through an angle which amounts to the sum of 180° and the angle of aperture of the fan-shaped beam.

The intensity of the X-rays received by the individual detector cells in any position or orientation of the X-ray source and the X-ray detector is digitized and applied to a reconstruction unit 4. In the reconstruction unit 4 this measured data is converted, after correction for known error sources and disturbances, into a density profile of the patient to be examined. For example, high and low density values in the density profile correspond to parts of the patient in which the X-ray absorption is high and low, respectively. The intensity values of the X-rays received by the X-ray detector in individual orientations constitute a respective density profile. Furthermore, an image of a slice along a plane through the patient can be derived from these density profiles by means of the reconstruction unit. An image of this kind may represent, for example, a cross-section of the patient to be examined. Such an image can be displayed on a monitor 14 which is coupled to the reconstruction unit. The image may also be stored as a digital image matrix or be applied to an image processing unit 15 for further processing.

The computer tomography device also includes a control unit 20 which serves to adjust the X-ray source. This adjustment concerns notably the adjustment of a high-voltage power supply 21 for the X-ray source, particularly the adjustment of the tube current and the high voltage whereby the intensity and the energy of the X-rays are adjusted. The control unit is connected to a memory unit 22 in which suitable reference adjustments of the X-ray source are stored for the examination of different parts of the anatomy of the patient to be examined. Such reference adjustments can be empirically determined by forming images of various parts of the anatomy of a large number of patients while using a number of adjustments of the X-ray source. The reference adjustments comprise the tube current and the high voltage of the X-ray source, and may also comprise other parameters of the computer tomography device, for example the slice thickness used, the speed of rotation of the X-ray source and the X-ray detector, and filter adjustments of the reconstruction unit. The reference adjustment preferably also comprises a reference thickness of the patient. The reference adjustments have been chosen in such a manner that in the circumstances represented by individual reference adjustments an image of the desired diagnostic quality is produced while using an acceptable X-ray dose.

Before the formation of density profiles of the patient to be examined, a so-called scanogram of the patient is formed by irradiating the patient by means of X-rays while the X-ray source and the X-ray detector are stationary and the patient table with the patient is displaced in the longitudinal direction of the patient. The reconstruction unit 4 derives from x-ray attenuation values density values of different parts of the patient from the local absorption of X-rays. These density values constitute the scanogram and are stored in the memory unit 22. The control unit 20 calculates the local thickness of the patient from the density values of the patient and compares the calculated thickness with the reference thickness. The control unit applies the calculated thickness of the patient and the reference thickness to a display 23. On the basis of the calculated thickness of the patient and the reference thickness the radiologist may decide to change the adjustment of the computer tomography device for the relevant examination in relation to the reference adjustment from the memory unit 22. Evidently, it is also possible for the control unit to provide the adjustment of the X-ray source automatically on the basis of the scanogram and the part of the patient to be examined.

The control unit 20 also includes one or more selection means 24, such as preset keys, for adjusting the computer tomography device so as to form the scanogram. This adjustment is performed by adjusting the X-ray source on the basis of the thickness of the patient. To this end, for example preset keys are provided for forming a scanogram of a small child, a thin, a normal and a very voluminous patient.

The noise in the X-ray image is a function of the adjustment of the X-ray source; in mathematically terms the standard deviation σ of the brightness values of the image is a function of the adjustment of the X-ray source p and the attenuation of the X-rays $$\mu d: \sigma = F(p, \mu d)$$

Therein, $\mu$ is the mean X-ray absorption coefficient along the path traveled by the X-rays through the part of the patient to be examined and d is the path length of the X-rays through the part of the patient to be examined. The standard deviation is an accurate measure of the noise level in the image.

Because the noise is a function of the adjustment of the X-ray source, the adjustment of the X-ray source is a function of the standard deviation:

$$p = G(\mu d, \sigma)$$

Notably when the noise level is caused mainly by the shot noise of the X-rays it holds that:

$$\sigma = \frac{c}{v} \frac{\sqrt{\exp(\mu d)}}{s I \tau}$$

where V is the electric high voltage, s is the slice thickness, I is the tube current, $\tau$ is the pulse duration of the X-ray source, and c is a proportionality constant.

An acceptable noise level $\sigma_{ref}$ can be empirically determined for adjustments p e.g. of the X-ray source and the reference thickness of the part of the patient $D_{ref}$ to be examined, for example by letting a number of radiologists evaluate a set of images formed by the computer tomography device in different circumstances. It has been found that the desired (or pre-determined) contrast resolution, and hence the acceptable (or pre-determined) noise level $\sigma_{ref}$, is dependent on the part of the patient being examined and also on the diagnostic requirements; therefore:

$$P_{ref,\alpha} = G(\mu D_{ref}, \sigma_{ref,\alpha})$$

This expression actually defines a reference patient, i.e. for a part of the patient to be examined, having the reference thickness $D_{ref}$, for an examination which is represented by the parameter $\alpha$ there is an adjustment $P_{ref}$ for which the image has a desired noise level, and hence a desired contrast resolution, with an acceptably low X-ray dose.

From the mean x-ray absorptivity of the part of the patient which is to be examined an effective patient thickness $D_{eff}$ is derived. For example $$D_{eff} = \frac{1}{\mu} \ln\left(\frac{I_0}{I}\right)$$

where $I_0/I$ is the ratio of the x-ray intensity incident on the part of the patient to be examined to the x-ray intensity passing through the part of the patient to be examined. This ratio is obtained from the scanogram. Thus the desired adjustment of the x-ray source is now calculated as $$p = G(\mu, D, \sigma_{ref})$$

It has been found that in practice the x-ray absorptivity of the patient $\mu$ is fairly approximated by the x-ray absorptivity of water. The effective patient thickness $D_{eff}$ may be calculated even more accurately by taking into account the mean x-ray absorptivities of the part of the patient to be examined in respective directions. The values of this ratio for different parts of the patient to be examined are taken up in the scanogram.

It has been found in practice that it is useful to display the effective patient thickness so that the radiologist can decide to adapt the adjustment of the X-ray source on the basis of the effective patient thickness and the reference thickness, notably on the basis of the difference therebetween.

All references cited herein, as well as the priority document European Patent Application 97201958.2 filed Jun. 29, 1998 are incorporated herein by reference in their entirety and for all purposes to the same extent as if each individual publication or patent or patent application was specifically and individually indicated to be incorporated by reference in its entirety for all purposes.

What is claimed is:

1. A computer tomography device, including
   an X-ray source,
   an X-ray detection system for picking up a number of density profiles of an object to be radiologically examined,
   a reconstruction unit for deriving an image signal from the density profiles, and
   a control system for deriving an adjustment of the x-ray source on the basis of a density value of a part of the object to be examined and of a pre-determined contrast resolution for the kind of tissue of the part of the object to be examined, and for adjusting the x-ray source according to the derived adjustment.

2. The device of claim 1 wherein the pre-determined contrast resolution for the kind of tissue depends on a pre-determined acceptable image noise level for the kind of tissue.

3. The device of claim 2 wherein the pre-determined acceptable noise level for the kind of tissue is empirically determined.

4. The device of claim 1 wherein the pre-determined contrast resolution for the kind of tissue depends on a noise index which depends on the image noise level.

5. A computer tomography device as claimed in claim 1 wherein the control system derives an adjustment of the X-ray source on the further basis of an orientation and/or position of the object relative to the X-ray source and the X-ray detection system.

6. A computer tomography device as claimed in claim 1 wherein the control system adjusts the intensity and/or the energy of the X-rays emitted by the X-ray source.

7. A computer tomography device as claimed in claim 6 wherein the control system adjusts the X-ray source by a reduction relative to a reference adjustment of the intensity and/or energy of the X-rays emitted by the X-ray source.

8. The device of claim 1 wherein the pre-determined contrast resolution differs for different kinds of tissue.

9. A computer tomography device, including
   an X-ray source,
   an X-ray detection system for picking up a number of density profiles of an object to be radiologically examined,
   a reconstruction unit for deriving an image signal from the density profiles, and
   a control system for (i) irradiating the object in order to measure a density value of a part of the object to be examined, the irradiating being adjusted on the basis of the thickness of the object, (ii) deriving an adjustment of the X-ray source on the basis of the measured density value of the part of the object and of the kind of tissue of the part of the object, and adjusting the X-ray source according to the derived adjustment.

10. The device of claim 9 wherein the control unit further comprises one or more selection means for indicating the thickness of the object.

11. A method of x-ray computed tomography comprising:
    deriving an adjustment of an x-ray source on the basis of a density value of a part of an object to be examined and of a pre-determined contrast resolution for the kind of tissue of the part of the object,
    adjusting the x-ray source according to the derived adjustment, irradiating the part of the object with x-rays from the x-ray source, picking-up a number of density profiles of the part of the object to be radiologically examined, and deriving an image signal from the density profiles.

12. The method of claim 11 wherein the pre-determined contrast resolution for the kind of tissue depends on a pre-determined acceptable image noise level for the kind of tissue.

13. The method of claim 11 wherein the pre-determined contrast resolution differs for different kinds of tissue.

14. A computer tomography device, including an X-ray source, an X-ray detection system for picking up a number of density profiles of an object to be radiologically examined, a reconstruction unit for deriving an image signal from the density profiles, a memory unit for storing one or more reference adjustments of the X-ray source, and a control system for adjusting the X-ray source a by taking into account (i) an adjustment derived on the basis of density value of a part of the object to be examined and of the kind of tissue of the part of the object to be examined and (ii) the reference adjustment stored in the memory unit.

15. A computer tomography device as claimed in claim 14 wherein the memory unit stores a plurality of reference adjustments, each reference adjustment being dependent on the kind of tissue of a part of the object to be examined.

16. A computer tomography device as claimed in claim 14 wherein the control system derives an adjustment of the X-ray source on the further basis of a difference between the derived adjustment and the reference adjustment.

17. A computer tomography device as claimed in claim 14 wherein the control system displays the derived adjustment and the reference adjustment, or displays the difference between the derived adjustment and the reference adjustment.

* * * * *